United States Patent [19]
Melker

[11] Patent Number: 5,242,410
[45] Date of Patent: Sep. 7, 1993

[54] WIRELESS HIGH FLOW INTRAVASCULAR SHEATH INTRODUCER AND METHOD

[75] Inventor: Richard J. Melker, Gainesville, Fla.

[73] Assignee: University of Florida, Gainesville, Fla.

[21] Appl. No.: 873,665

[22] Filed: Apr. 23, 1992

Related U.S. Application Data

[63] Continuation of Ser. No. 685,603, Apr. 15, 1991, abandoned.

[51] Int. Cl.⁵ .............................................. A61M 5/00
[52] U.S. Cl. .................................................... 604/164
[58] Field of Search ................ 604/51, 52, 53, 164, 604/158, 159, 161, 165, 169, 170; 606/191

[56] References Cited

U.S. PATENT DOCUMENTS

| | | | |
|---|---|---|---|
| 3,352,306 | 11/1967 | Hirsch | 604/164 |
| 3,565,074 | 2/1971 | Foti et al. | 128/214.4 |
| 4,230,123 | 10/1980 | Hawkins, Jr. | 128/658 |
| 4,581,019 | 4/1986 | Curelaru et al. | 604/164 |
| 4,629,450 | 12/1986 | Suzuki et al. | 604/164 |
| 4,772,264 | 9/1988 | Cragg | 604/158 |
| 4,911,691 | 3/1990 | Aniuk et al. | 604/164 |
| 4,978,334 | 12/1990 | Toye et al. | 604/51 |
| 4,994,027 | 2/1991 | Farrell | 604/164 |
| 4,995,866 | 2/1991 | Amplatz et al. | 604/53 |

*Primary Examiner*—Paul J. Hirsch
*Attorney, Agent, or Firm*—Spensley Horn Jubas & Lubitz

[57] ABSTRACT

A wireless high flow sheath introducer for intravascular access and a method for using such an introducer. The invention comprises a large bore flow sheath having a nested, coaxial, tapered dilator which dilates a vein to a size sufficient for introduction of the large bore flow sheath, and a needle nested within the tapered dilator and coaxial therewith for initially piercing the target vessel. The present invention also provides a method of using such an instrument.

17 Claims, 1 Drawing Sheet

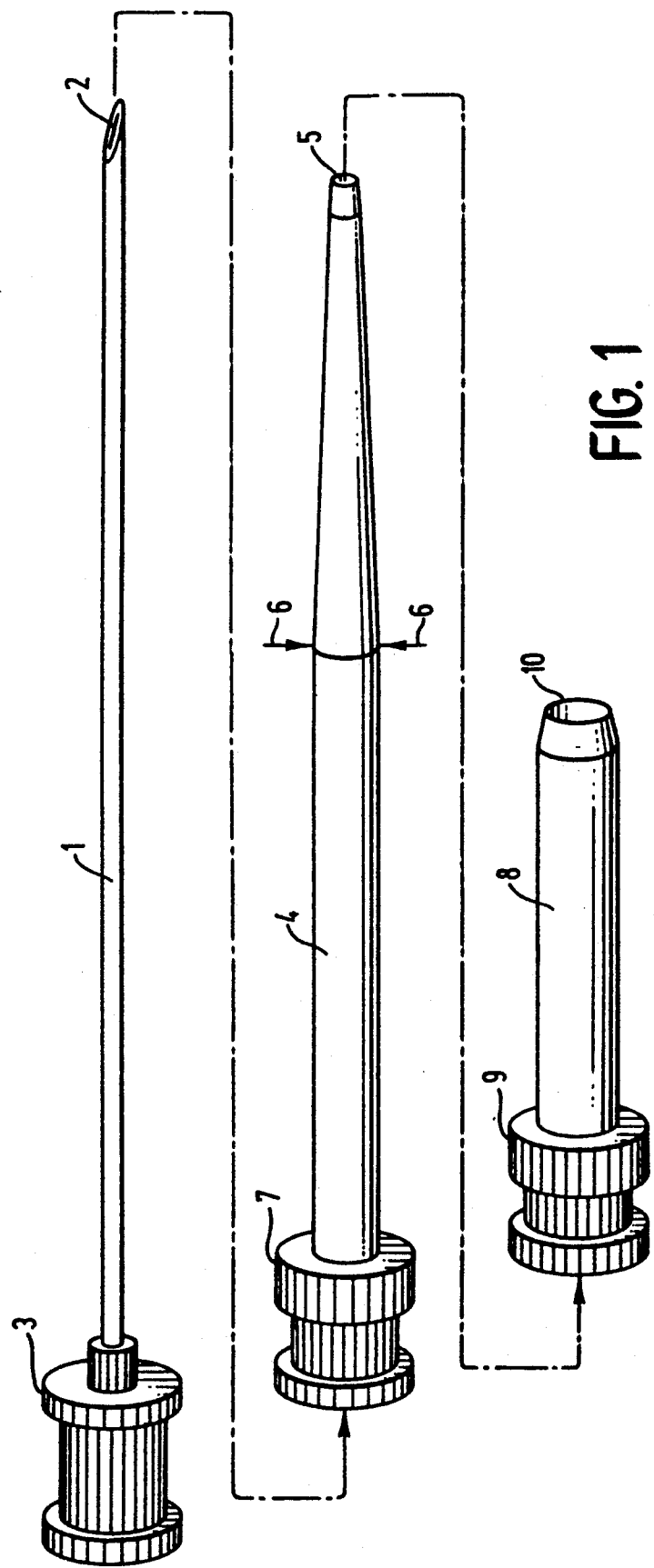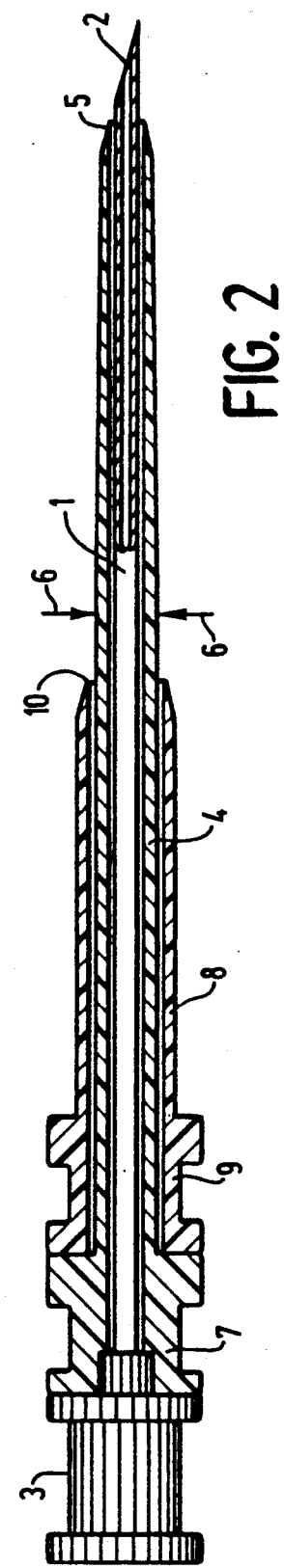

WIRELESS HIGH FLOW INTRAVASCULAR SHEATH INTRODUCER AND METHOD

This is a continuation of application Ser. No. 07/685,603 filed on Apr. 15, 1991, now abandoned.

BACKGROUND OF THE INVENTION

1. Field of the Invention

This invention relates to intravascular access devices, and more particularly, to a wireless high flow sheath introducer for intravascular access and a method for using such an introducer.

2. Description of Related Art

There are several methods for introducing a catheter into a blood vessel. In general, in order to introduce a catheter into a blood vessel through the skin, the practice in the prior art is to use an introducing needle, a guidewire, and a dilator (this technique is commonly referred to as the "Seldinger Technique"). More specifically, the introducing needle (which may compromise an inner needle portion and a cover tube, or alternatively, just the needle portion) is used to pierce the desired blood vessel. In the instance where both the inner needle portion and a cover tube are used, the inner needle portion is withdrawn. The guidewire is then inserted into the blood vessel by passing it through the cover tube. In the instance where only the needle portion is used, the needle is left in place, and the guidewire is then inserted into the blood vessel by passing it through the needle. This is followed by withdrawing the cover tube or the needle, leaving the guidewire in place. Next a dilator is introduced so as to fit over the guidewire. The dilator functions to dilate the opening made in the subcutaneous tissue and in the wall of the blood vessel, thus, making it possible to reduce resistance which the catheter would otherwise meet in being inserted through the subcutaneous tissue and the blood vessel wall. Next, the dilator is withdrawn from the guidewire and a catheter is fitted over the guidewire so that the catheter may be then introduced into the blood vessel.

The conventional method described above is disadvantageous, especially in emergency situations, in that the preparation and handling of the instruments is of some complexity. The Seldinger Technique is time consuming and requires the use of an introducing needle, which makes it possible to insert a guidewire into the blood vessel so that the catheter can be introduced into the blood vessel through the skin, as well as a dilator for spreading the subcutaneous tissue and the opening in the blood vessel wall to facilitate the introduction of the catheter. The procedure requires a large sterile field to prevent contamination and introduction of infection during insertion and removal of the multiple parts.

The problem of properly introducing a catheter into a blood vessel becomes more acute in emergency situations, where the catheter must be introduced quickly and sterilely and where a high-flow rate is required. For example, intravenous access is a vital step in the resuscitation of patients in hypovolemic shock. Until recently, plastic over-the-needle catheters were used for peripheral venous insertion, and plastic catheters placed through needles (intercaths) were used for insertion into the central venous circulation. Recently, it has been recognized that these catheters often do not infuse fluids at a high enough flow rate for the resuscitation of severely hypovolemic patients.

In addition to being used for the placement of intravascular catheters, the Seldinger Technique is also used for the introduction of "catheter introducers". These introducers are placed in the vessel so that catheters can be moved in and out of the vessel without losing patency between the skin and blood vessel, and eliminate the need to reintroduce a guidewire. These "catheters introducers" are introduced over a guidewire as previously described. However, the "catheter introducer" is coaxially loaded over the dilator for insertion. The dilator extends approximately two to three centimeters distal to the "catheter introducer". Thus, the dilator with the catheter introducer loaded over it is advanced over the guidewire through the subcutaneous tissue and into the vessel. Initially, only the dilator is advanced to make a hole of sufficient size to allow introduction of the "catheter introducer". Then, the dilator is further advanced until both the dilator and "catheter introducer" are in the blood vessel. The guidewire and dilator are then removed, leaving the "catheter introducer" in the vessel. Thus, patency between the skin and the lumen of the vessel is guaranteed. Catheters of various sizes and lengths can be introduced through the "catheter introducer" and can be changed without losing patency of the vessel.

It was soon recognized that these large bore "catheter introducers" could be placed in vessels to allow the infusion of large volumes of fluid at very high flow rates. Recently, high flow, large bore peripheral sheaths, similar to catheter introducers, have been developed. These high flow large bore sheaths are designed for placement by the Seldinger Technique. These sheaths deliver flow rates between 2.5 and 5 times greater than catheters previously used for peripheral and central infusions.

Unfortunately, many physicians are unskilled in the Seldinger Technique of placing a sheath over a guidewire. It has become evident that the lack of sufficient psychomotor skill limits the use of these new high flow devices to physicians with previous experience in inserting devices over guidewires. It therefore would be advantageous to provide a high flow catheter introducing instrument that does not require placing a sheath over a guidewire. The present invention provides such an instrument and a method for using such an instrument. Additionally, the present invention provides an instrumental that can be rapidly placed in peripheral vessels without the necessity of a large sterile field, which is needed when high flow catheters are placed over guidewires. Thus, the present invention provides an instrument which is ideal for use in emergency conditions where large sterile fields are rarely possible.

SUMMARY OF THE INVENTION

The invention comprises a wireless high flow sheath introducer set which combines the ease of insertion of a peripheral intravascular catheter with the high flow characteristics of an intravascular sheath. This is accomplished by the use of a three-piece introducer set comprising a large bore flow sheath having a nested, coaxial, tapered dilator which dilates a vein to a size sufficient for introduction of the large bore flow sheath, and a hypodermic needle nested within the tapered dilator and coaxial therewith for initially piercing the target vessel. The inventive instrument is simple enough to permit insertion even in a pre-hospital setting by medical personnel of average skill. Early resuscitation with large volumes of fluid can improve survival in patients with hypovolemic shock.

The present invention also provides a method of using such an instrument.

The details of the preferred embodiment of the present invention are set forth in the accompanying drawings and the description below. Once the details of the invention are known, numerous additional innovations and changes will become obvious to one skilled in the art.

BRIEF DESCRIPTION OF THE DRAWINGS

FIG. 1 is an exploded perspective view of a wireless high flow sheath introducer set in accordance with the present invention.

FIG. 2 is a cross-sectional elevation view of the wireless high flow sheath introducer set of the present invention, with all pieces nested and ready for initial insertion.

Like reference numbers and designations in the drawings refer to like elements.

DETAILED DESCRIPTION OF THE INVENTION

Throughout this description, the preferred embodiment and examples shown should be considered as exemplars, rather than limitations on the present invention.

STRUCTURE OF THE INSTRUMENT

As shown in FIG. 1, the wireless high flow sheath introducer set consists of three parts. The innermost part preferably comprises a solid or hypodermic needle 1 approximately 2.5 to 3 inches in length. The needle 1 preferably consists of a stainless steel shaft and the distal end 2 is of course sharpened to medical standards. In the preferred embodiment, the needle 1 includes a connecting hub 3 at its proximal end, such as a plastic Luer-lock hub or other friction fitting connector. In the preferred embodiment of the invention, the needle 1 is a 19-gauge hypodermic needle, having an interior diameter (ID) of approximately 0.027 inches and an outside diameter (OD) of approximately 0.042 inches.

The second part of the introducer set consists of a dilator 4 which is placed over the needle 1 at the initial stage of insertion, so that the needle 1 is coaxial with the dilator 4. The dilator 4 has an ID slightly greater than the OD of the needle 1, and is tapered at its distal end 5 to form a tight, virtually transitionless fit just proximal to the sharpened distal end 2 of the needle 1. In the preferred embodiment of the invention, the distal end 5 of the dilator 4 has an OD of approximately 0.050 inches, widening proximally over approximately one-third of its length to an OD in the range of about 0.079 to 0.118 inches at a transition point 6. The dilator 4 is preferably in the range of 0.75-1.0 inches in length from its distal end 5 to the transition point 6. Proximal of the transition point 6, the dilator 4 has an approximately uniform diameter from the transition point 6 to a proximal connecting hub 7, such as a Luer-lock hub or other friction fitting connector. The dilator 4 is preferably approximately 2 to 2.5 inches in total length, and is preferably made entirely of sterilizable plastic.

The third piece of the introducer set comprises a high flow intravascular sheath 8 which is designed to be positioned over the proximal two-thirds of the dilator 4 (that is, from the connecting hub 7 to the transition point 6), so that the dilator 4 is coaxial with the intravascular sheath 8. In the preferred embodiment, the sheath 8 is approximately 1 to 1.5 inches in length. On its proximal end 9, the intravascular sheath 8 has a connecting hub 9 designed to mate with standard intravascular catheter sets (for example, by means of a standard female Luer-lock adaptor hub). The distal end 10 is preferably beveled to form a transitionless fit onto the dilator 4. The intravascular sheath 8 is preferably made entirely of sterilizable plastic. In the preferred embodiment of the invention, the intravascular sheath 8 has an ID slightly greater than the OD of the dilator at the transition point 6, and an OD of approximately 0.120–0.134 inches.

FIG. 2 shows a cross-sectional view of the inventive introducer set with all three components parts "nested" together. The distal end of the set comprises the sharpened distal end 2 of the needle 1. Proximal of the sharpened distal end 2 of the needle 1, the tapered distal end 5 of the dilator 4 is beveled so as to form a virtually transitionless fit around the shaft of the needle 1. The widening of the dilator 4 proximally to the transition point 6 provides a continuation of such a transitionless fit to the beveled edges 10 of the intravascular sheath 8. In the preferred embodiment, the entire length of the assembled introducer set structure is 3 inches or less, for ease of use and handling. With the preferred range of dimensions for the introducer set, the degree of taper for the dilator 4 from its distal end 5 to the transition point 6 is preferably in the range of about 1.26° to about 5.18° (a slope of about 0.022 to about 0.09) for a straight-sided dilator 4. This range of slopes has been found to provide a suitable degree of gentle entry into a vessel, while permitting the introducer set to be of reasonable length.

OPERATIONAL CYCLE

In use, the inventive wireless high flow sheath introducer set is used as follows. An appropriate vessel, such as that found in the forearm or antecubital fossa, is located and distended by placing a tourniquet proximal to the insertion site. The site of insertion is cleansed with an antiseptic agent, such as alcohol, and a small nick is made to the skin by means of a scalpel at the insertion site to ease insertion of the intravascular sheath 8. The inventive device is inserted with the three elements "nested" together. The vessel is initially entered with the sharpened distal end 2 of the needle 1. As the needle is advanced, the tapered distal end 5 of the dilator 4 enters the vessel in a manner identical to placement of an intravenous plastic catheter. As the dilator 4 is further advanced into the vessel, the needle 1 is retracted into the dilator 4 to prevent laceration of the wall of the vessel as the dilator is further advanced. The dilator 4 is passed into the vessel with a reciprocating motion until the distal end 10 of the intravascular sheath 8 is also within the vessel. The intravascular sheath 8 is then further advanced into the vessel as the dilator 4 and needle 1 are withdrawn from the interior of the sheath 8. Thus, a high flow intravascular sheath is introduced into the vessel in a manner similar to the introduction of a much smaller bore intravascular catheter. The only additional step required for insertion of the high flow intravascular sheath 8 of the inventive device is a small nick in the skin with a scalpel blade to ease the insertion of the large bore device.

A number of embodiments of the present invention have been described. Nevertheless, it will be understood that various modifications may be made without departing from the spirit and scope of the invention. For example, although a straight taper is shown for the dilator 4, a slight concave curve from the distal end 5 to the transition point 6 of the dilator 4 can also be used. Such a concave shape can be imparted by standard plastic forming techniques known in the medical device industry. As another example, although the preferred embodiment of the invention is made of disposable elements, including sterilizable plastic, the component parts of the invention can be made of other materials, and be made for repeated sterilization and use. Accordingly, it is to be understood that the invention is not to be limited by the specific illustrated embodiments, but only by the scope of the intended claims.

I claim:

1. A wireless, high-flow intravascular sheath introducer comprising:
   a. a high-flow intravascular sheath sized to fit within an intravascular body vessel, and having a passage therethrough for fluid flow and a sheath connector hub attached to its proximal end,
   b. an essentially rigid dilator, removably mountable coaxially within the passage of the intravascular sheath through the proximal end of the sheath, the dilator having a passage therethrough and being positionable within the sheath so that a substantial length of the dilator projects from the distal end of the sheath at a transition point, the dilator having a distal end spaced apart from the transition point;
   c. a small-diameter needle sized to penetrate an intravascular body vessel, removably mounted coaxially within the passage of the dilator through the proximal end of the dilator, the needle having a sharpened distal end for piercing a body vessel, the needle being positionable within the dilator so that the sharpened distal end projects from the distal end of the dilator;

and further characterized by:
   d. the dilator having an inner diameter closely approximating the outer diameter of the needle, a largest outer diameter at the transition point between the sheath and the dilator closely approximating the inner diameter of the sheath, and a smallest outer diameter at its distal end closely approximating the outer diameter of the needle;
   e. the dilator tapering inwardly with a transitionless angled slope distally from the transition point between the sheath and the dilator to its distal end, and the dilator terminating just proximal to the sharpened distal end of the needle, the distal end of the dilator closely conforming to the shape of the needle to facilitate penetration of the dilator into a body vessel pierced by the needle;

wherein the dilator is movable from a position whereby the sharpened distal end of the needle is exposed to a position whereby the sharpened distal end of the needle is shielded.

2. The wireless, high-flow intravascular sheath introducer of claim 1, wherein the sheath has a length approximately two-thirds the length of the dilator.

3. The wireless, high-flow intravascular sheath introducer of claim 1, wherein the dilator has a length such that approximately one-third of the dilator projects from the distal end of the sheath.

4. The wireless, high-flow intravascular sheath introducer of claim 1, wherein the dilator has a slope from its distal end to the transition point in the range of about 0.022 to about 0.09.

5. The wireless, high-flow intravascular sheath introducer of claim 1, wherein the dilator has a concave contour from its distal end to the transition point.

6. The wireless, high-flow intravascular sheath introducer of claim 1, wherein the distal end of the sheath is beveled to closely conform to the shape of the dilator to facilitate penetration of the sheath into a body vessel penetrated by the dilator.

7. The wireless, high-flow intravascular sheath introducer of claim 1, further including a dilator connector hub attached to the proximal end of the dilator.

8. The wireless, high-flow intravascular sheath introducer of claim 1, further including a needle connector hub attached to the proximal end of the needle.

9. A method of positioning a high-flow intravascular sheath within an intravascular body vessel, without using a guide wire, comprising the steps of:
   a. providing an assembled wireless, high-flow intravascular sheath introducer of the type of claim 1;
   b. piercing the outer wall of a selected intravascular body vessel with the sharpened distal end of the needle;
   c. advancing the needle into the vessel until the distal end of the dilator penetrates the wall of the vessel, then retracting the sharpened distal end of the needle within the passage of the dilator to shield the needle and prevent laceration of the wall of the vessel;
   d. advancing the dilator within the vessel until the distal end of the sheath penetrates the wall of the vessel, then withdrawing the needle and dilator from the passage of the sheath as the sheath is completely advanced into the vessel wherein the needle remains shielded upon withdrawal.

10. The method of claim 9, including the further step of incising the skin adjacent a selected body vessel to ease insertion of the sheath into the vessel.

11. The method of claim 9, wherein the sheath has a length approximately two-thirds the length of the dilator.

12. The method of claim 9, wherein the dilator has a length such that approximately one-third of the dilator projects from the distal end of the sheath.

13. The method of claim 9, wherein the dilator has a slope from its distal end to the transition point in the range of about 0.022 to about 0.09.

14. The wireless, high-flow intravascular sheath introducer of claim 9, wherein the dilator has a concave contour from its distal end to the transition point.

15. The method of claim 9, wherein the distal end of the sheath is beveled to closely conform to the shape of the dilator to facilitate penetration of the sheath into a body vessel penetrated by the dilator.

16. The method of claim 9, wherein the dilator further includes a dilator connector hub attached to the proximal end of the dilator.

17. The method of claim 9, wherein the needle further includes a needle connector hub attached to the proximal end of the needle.

* * * * *